United States Patent [19]

Kenneally

[11] Patent Number: 5,491,226

[45] Date of Patent: Feb. 13, 1996

[54] PROCESS FOR PREPARING POLYOL POLYESTERS HAVING LOW LEVELS OF TRIGLYCERIDES

[75] Inventor: Corey J. Kenneally, Maineville, Ohio

[73] Assignee: Procter & Gamble Company, Cincinnati, Ohio

[21] Appl. No.: 223,624

[22] Filed: Apr. 6, 1994

[51] Int. Cl.$^6$ .............. C07H 1/00; C07H 13/06; C07H 13/12; C07H 15/04

[52] U.S. Cl. .............. 536/115; 536/116; 536/119; 536/120; 536/124

[58] Field of Search .................... 536/115, 116, 536/119, 120, 124

[56] References Cited

U.S. PATENT DOCUMENTS

| | | | |
|---|---|---|---|
| 2,177,407 | 10/1939 | Hansley | 554/167 |
| 2,290,609 | 7/1942 | Goss et al. | 554/168 |
| 2,360,844 | 10/1944 | Bradshaw et al. | 554/156 |
| 2,383,580 | 8/1945 | Arrowsmith et al. | 554/167 |
| 2,383,596 | 8/1945 | Dreger | 554/167 |
| 2,383,614 | 8/1945 | Percy | 554/175 |
| 2,383,633 | 8/1945 | Trent | 554/167 |
| 3,054,789 | 9/1962 | D'Amato | 536/119 |
| 3,349,081 | 10/1967 | Nobile | 536/119 |
| 3,951,945 | 4/1976 | Heesen et al. | 536/18.5 |
| 3,996,206 | 12/1976 | Parker et al. | 536/119 |
| 4,104,464 | 8/1978 | James | 536/115 |
| 4,327,183 | 4/1982 | Masuda et al. | 435/274 |
| 4,371,470 | 2/1983 | Matsukura et al. | 554/167 |
| 4,521,595 | 6/1985 | Stühler et al. | 536/127 |
| 4,582,946 | 4/1986 | Rogier | 568/853 |
| 4,927,920 | 5/1990 | Wagner et al. | 536/119 |
| 4,954,621 | 9/1990 | Masaoka et al. | 536/119 |
| 4,966,966 | 10/1990 | Wada et al. | 536/119 |
| 4,968,791 | 11/1990 | Van der Plank | 536/119 |
| 4,973,489 | 11/1990 | Meyer et al. | 426/611 |
| 5,043,438 | 8/1991 | Buter | 536/119 |
| 5,071,669 | 12/1991 | Seiden | 426/660 |
| 5,071,975 | 12/1991 | Ver der Plank et al. | 536/119 |
| 5,079,355 | 1/1992 | Grechke et al. | 536/119 |

OTHER PUBLICATIONS

T995,002; Jun. 3, 1980; Zeringue, Jr. et al.; 210/23; U.S. Defensive Publication.

Primary Examiner—Michael G. Wityshyn
Assistant Examiner—Everett White
Attorney, Agent, or Firm—Rose Ann Dabek; T. M. Rosnell; J. C. Rasser

[57] ABSTRACT

A process for preparing polyol fatty acid polyesters having levels of triglyceride below 0.5% is described. Methyl esters having a level of monoglycerides below 500 ppm, a non-detectable level of di- and triglyceride and a glycerine level of less than about 200 ppm are prepared and then used in a two-stage, solvent-free transesterification reaction to prepare the polyol fatty acid polyesters.

14 Claims, No Drawings

PROCESS FOR PREPARING POLYOL POLYESTERS HAVING LOW LEVELS OF TRIGLYCERIDES

TECHNICAL FIELD

The present invention relates to a process for preparing polyol polyesters which contain very low levels of triglyceride. Such polyol polyesters are "fat-free".

BACKGROUND OF THE INVENTION

Certain polyol fatty acid polyesters have been suggested as low or reduced calorie substitutes for triglyceride fats and oils used in foods. For example, nonabsorbable, nondigestible sugar fatty acid esters or sugar alcohol fatty acid esters having at least 4 fatty acid esters groups with each fatty acid having from 8 to 22 carbon atoms have been used as partial or full fat replacers in low calorie food compositions. See Mattson and Volpenhein; U.S. Pat. No. 3,600,186; Issued Aug. 17, 1971. Likewise, certain intermediate melting polyol polyesters have been developed that provide passive oil loss control, while at the same time reducing waxiness in the mouth. See Bernhardt; European Patent Application Nos. 236,288 and 233,856; Published September 9, and Aug. 26, 1987, respectively. Blends of completely liquid polyol polyesters with completely solid polyol polyester hardstocks, preferably esterified with $C_{10}$ to $C_{22}$ saturated fatty acids (e.g. sucrose octastearate) have also been proposed in order to provide passive oil loss control. See for example, Jandacek; U.S. Pat. No. 4,005,195; and Jandacek/Mattson; U.S. Pat. No. 4,005,196; Both issued Jan. 25, 1977.

A number of different processes have been disclosed in the art for preparing highly esterified polyol fatty acid polyesters, in particular sucrose polyesters, useful as reduced calorie fat substitutes. One such process for preparing these polyesters involves a solvent-free, essentially two-step transesterification of the polyol (e.g., sucrose) with the fatty acid esters of an easily removable alcohol (e.g., fatty acid methyl esters). In the first step, a mixture of sucrose, methyl esters, alkali metal fatty acid soap and a basic esterification catalyst are heated to form a melt. The amount of methyl esters is such that the melt forms primarily partial fatty acid esters of sucrose, e.g., sucrose mono-, di- and/or triesters. In the second step, an excess of methyl esters are added to this melt which is then heated to convert the partial sucrose esters to more highly esterified sucrose polyesters, e.g., sucrose hexa-, hepta-, and particularly octaesters. See, for example, U.S. Pat. No. 3,963,699 (Rizzi et al.), issued Jun. 15, 1976; U.S. Pat. No. 4,517,360 (Volpenhein), issued May 14, 1985; and U.S. Pat. No. 4,518,772 (Volpenhein), issued May 21, 1985, which disclose solvent-free, two-step transesterification processes for preparing highly esterified polyol fatty acid polyesters, in particular highly esterified sucrose polyesters.

In some processes for preparing highly esterified polyol fatty acid polyesters, all of the fatty acid methyl esters are added to the polyol (e.g., sucrose) at the beginning of the reaction, i.e. a one-step addition process. See, for example, U.S. Pat. No. 4,611,055 (Yamamoto et al.), issued Sep. 9, 1986. Like the previously described two-step processes, such one-step processes first form primarily partial fatty acid esters of sucrose that are then converted to more highly esterified sucrose polyesters. Accordingly, these single-step and two-step processes are collectively referred to hereinafter as "two-stage" transesterifications, wherein the "first stage" involves the formation of the partial esters and wherein the "second stage" involves the conversion of the partial esters to more highly esterified polyesters.

Alternatively, highly esterified polyol polyesters may be prepared by two stage solvent-based processes, (see, for example, U.S. Pat. No. 4,954,621 (Masaoka et al.), or one stage solvent-based or solvent free processes, see for example, U.S. Pat. No. 4,968,791, (Van Der Plank), issued Nov. 6, 1990; U.S. Pat. No. 5,079,355 (Meszaros Grechke et al.) issued Jan. 7, 1992; or U.S. Pat. No. 5,071,975 (Ver der Plank et al.) issued Dec. 10, 1991.

The methyl esters which are used to prepare the polyol polyesters can be prepared by the transesterification of triglyceride oils and fats with methanol in the presence of an alkaline catalyst. After the transesterification reaction, a crude glycerine layer comprising glycerol formed in the transesterification reaction, soap formed by the catalyst, catalyst, some methyl esters and methanol, is separated from the fatty-acid methyl ester layer. The methyl ester layer is then purified by any suitable recovery method, such as e.g. distillation. Processes of this type have been described in U.S. Pat. Nos. 2,383,596, 2,383,579, 2,383,580, 2,383,596, 2,383,599 2,383,601, 2,383,602, 2,383,614, 2,383,632 and 2,383,633 and in the European Pat. No. 0 164 643. An extra esterification step before recovery, but after separation of the fatty acid methyl ester layer from the glycerol layer may optionally be used to produce high yields of high purity fatty acid methyl esters. See European Pat. No. 391 485.

Unfortunately, the methyl esters prepared by any of these known processes are likely to contain some residual level of fat sources such as glycerine, and mono-, di-, or triglyceride. When these fat-containing methyl esters are used to prepare polyol fatty acid polyesters, they will cause the polyol polyester product to contain undesirably high levels of triglyceride fat. Although the triglyceride fat is typically present in the polyol polyesters at levels below 2%, these triglycerides nevertheless add calories to the polyol polyester and keep the polyol fatty acid polyesters from being completely fat-free. It is, therefore, an object of the present invention to prepare methyl esters containing minimal levels of glycerine and mono-, di-, and triglyceride for use in preparing polyol polyesters having a triglyceride level of less than 0.5%.

Another disadvantage with known processes for preparing methyl esters is that on a production scale an excessively high level of residue is formed on the bottom of the still or distillation apparatus during ester distillation. Typically, glycerine levels of 1 to 1½% are present in methyl esters even after esterification and gravity decanting of the glycerine layer as a result of difficulty in coalescing substantially all of the glycerine in a production scale settling tank. If glycerine is not effectively separated from the methyl esters either through centrifugation, extraction or absorption, before heat treatment and/or distillation, substantial levels of di-glycerides and tri-glycerides will form, possibly in excess of 10% of the methyl ester. Di-glycerides and tri-glycerides are not volatile and remain in the residue at the bottom of the still.

It is, therefore, another object of this invention to ensure that a minimal level of glycerine is present in the methyl ester prior to the distillation in order to minimize the amount of residue during the distillation to less than 10%, and preferably less than 5%. This offers advantages in minimizing still bottom recycle streams as well as maximizing finished product yields in ester-making processes.

SUMMARY OF THE INVENTION

The present invention relates to a process for preparing polyol fatty acid polyesters which contain less than about 0.5% triglycerides.

Such a process comprises the steps of preparing fatty acid methyl esters having a level of monoglycerides below 500 ppm, a nondetectable level of di- and triglyceride and a glycerine level of less than 200 ppm and then transesterifying these fatty acid methyl esters with a polyol in a solvent-free, two-stage process. The methyl ester-making process preferably has a yield loss from still bottom residue of less than 10%.

The fatty acid methyl esters can be prepared by first reacting a fatty acid glycerol ester with a monohydric lower alkyl alcohol in the presence of a suitable catalyst to produce a mixture of fatty acid methyl esters, fatty acid glycerol esters and glycerol. This mixture can then separated into a glycerine-rich layer and a fatty acid methyl ester-containing layer. The fatty acid methyl ester-containing layer must have a level of residual mono-, di-, and tri- glycerides below about 2.5% by weight before proceeding to the next step when this method is used. When the appropriate levels of mono-, di-, and triglycerides has been realized, the fatty acid methyl ester-containing layer can be water washed under condition suitable to provide a fatty acid methyl ester phase containing less than about 300 ppm glycerine. Then, the fatty acid methyl ester layer can be distilled to provide the desired fatty acid methyl esters.

Once the fatty acid methyl esters having the appropriate levels of mono-, di-, and triglycerides and glycerine have been formed the fatty acid methyl esters are transesterified with a polyol to form highly esterified polyol fatty acid polyesters which contain less than about 0.5% triglycerides.

DETAILED DESCRIPTION OF THE INVENTION

The process of the present invention, as well as the materials used therein, are described in detail as follows:

A. Preparation of Fatty Acid Methyl Esters

The first step in the process of the present invention is to prepare fatty acid methyl esters having a monoglycerides level of less than about 500 ppm, a nondetectable level of di- and triglycerides and a glycerine level of less than about 200 ppm. Such fatty acid methyl esters can be prepared as follows:

1. Reacting a Fatty Acid Glycerol Ester with a Monohydric Lower Alkyl Alcohol in the Presence of a Suitable Catalyst to Produce a Mixture of Fatty Acid Methyl Ester, Fatty Acid Glycerol Esters and Glycerol As a first step in preparing fatty acid methyl esters having the characteristics hereinbefore described, a fatty acid glycerol ester is reacted with a monohydric lower alcohol in the presence of a suitable catalyst to produce a mixture comprising, as main components, fatty-acid lower-alkyl monoesters and glycerol. In addition, the mixture will comprise unreacted or partially reacted fatty-acid glycerol esters, remaining catalyst, soap and lower-alkyl alcohol.

Suitable fatty-glycerol esters which include mono-, di- and triglycerides, can be derived from either synthetic or natural, saturated or unsaturated fatty acids and include positional and geometrical isomers. Suitable preferred saturated fatty acids for use in preparing the fatty glycerol esters to be used in the process of the present invention include, for example, acetic, butyric, caproic, caprylic, caprio, lauric, myristic, palmitic, stearic, arachidic, behenic, isomyristic, isomargaric, hydroxystearic, and anteisoarachadic. Suitable preferred unsaturated fatty acids for use in preparing the fatty glycerol esters to be used in the process of the present invention include, for example, myristoleic, palmitoleic, ricinoleic, linoleic, oleic, elaidic, linolenic, eleosteric, arachidonic, erucic, and erythrogenic acids. The fatty acids can be used "as is," and/or after hydrogenation, and/or isomerization, and/or purification. Typically, a mixture of glycerides consisting primarily of triglycerides fats and oils obtained from animal or vegetable sources is used as the fatty glycerol ester in the process of the present invention. Suitable triglycerides fats and oils specifically include soybean oil, palm oil, cottonseed oil, safflower oil, rapeseed oil (high erucic acid), canola (low erucic acid), and corn oil.

Suitable monohydric lower alkyl alcohols for use in preparing the methyl ester used in the process of the present invention include $C_1$ to $C_5$ mono-alcohols. Methanol is an especially preferred alcohol for use in the process of the present invention.

Suitable basic catalysts for use in preparing the methyl esters used in the process of the present invention include alkali metals such as sodium, lithium and potassium, alloys of two or more alkali metals, such as sodium-lithium and sodium-potassium alloys; alkali metal hydrides, such as sodium, lithium and potassium hydride; alkali metal lower ($C_1$–$C_4$) alkyls such as butyl lithium; and alkali metal alkoxides of lower ($C_1$–$C_4$) alcohols, such as lithium methoxide, potassium t-butoxide, potassium methoxide, and/or sodium methoxide. Sodium methoxide is an especially preferred catalyst for use herein.

The reaction between the fatty acid glycerol ester and the monohydric lower alkyl alcohol can be carried out using conventional transesterification/alcoholysis conditions. In general the reaction will be carried out at elevated temperature, which dependent upon the particular (blend of) fatty acid residues and alcohol involved may range from about 20° to about 160° C., typically from about 30° to about 120° C., more typically from about 40° to about 80° C. It may be convenient to carry out the reaction under conditions of refluxing or alternatively in a closed reaction vessel to maintain the desired temperature and/or pressure regime. Such pressures may be atmospheric as well as sub- or super-atmospheric. Preferably, some agitation is applied to the reactants, e.g. by stirring the reaction mixture.

In general a stoichiometric excess of the monohydric lower-alkyl alcohol with respect to the fatty acid residues in the one or more fatty-acid glycerol esters is used. Typically, molar ratios of monohydric lower-alkyl alcohol to glycerol ester fatty-acid residues are greater than 1.5:1. Excess amounts corresponding to a molar ratio of between 2:1 and 6:1 are preferred.

A relatively small amount of catalyst can be used. Suitable amounts generally range from about 0.002 to about 1 mole per kg of reaction mixture. Preferred amounts &catalyst range from about 0.01 to about 0.1 mole per kg of reaction mixture, amounts of from 0.02 to 0.05 mole per kg are most preferred.

Using the above described transesterification conditions suitable reaction times range from about 10 minutes to several hours, preferably from about 30 minutes to about 3 hours.

2. Separating the Mixture Produced in Step (1) into a Glycerine Phase and a Fatty Acid Methyl Ester-Containing Phase At a sufficiently high degree of conversion to fatty-acid methyl ester, the reaction mixture is separated into a lower-layer rich in glycerol and an upper-layer rich in the fatty acid methyl-ester. This separation can be accomplished by conventional means including, for example, gravity decanting or centrifuging.

The fatty acid methyl ester-containing phase preferably comprises at least about 80%, preferably at least about 90%, more preferably at least about 95% fatty acid methyl ester. The fatty acid methyl ester-containing phase can also contain fatty acid glycerol esters (e.g., mono-, di- and triglycerides), soap, lower alkyl alcohol and catalyzing agent. The level of glycerides present in the fatty acid methyl ester-containing phase must be less than about 2.5%, preferably less than about 1.5%, more preferably less than about 1% before proceeding to the next step.

If, upon analysis, the level of glycerides in the fatty acid methyl ester-containing phase is greater than 2.5%, steps (1) and (2) should be repeated as necessary, using substantially less lower alkyl alcohol and catalyst, to provide a fatty acid methyl ester-containing phase having the appropriate characteristics.

3. Water Washing the Fatty Acid Methyl Ester-Containing Phase

After the hereinbefore described esterification reaction has been brought to substantial completion such that the fatty acid methyl ester-containing phase contain less than 2.5% of glycerides, said fatty acid methyl ester-containing phase is subjected to a water washing step to extract residual glycerine, soap and catalyst from the fatty acid methyl ester-containing phase. This water washing step comprises washing the fatty acid methyl ester-containing phase with water under conditions suitable to provide a fatty acid methyl ester phase containing less than 300 ppm glycerine, preferably less than 50 ppm glycerine. When the fatty acid methyl ester phase contains less than 300 ppm glycerine at this stage, the amount of residue during the distillation step (described hereinafter) will be less than 10%, preferably less than 5%.

Typically, from about 2% to about 50% by weight of water is added to the fatty acid methyl ester-containing phase in a stirred tank, a column or an in-line static mixer for from about 0.5 minutes to about 60 minutes at a temperature of from about 21.1° C. (70° F.) to about 93.3° C. (200° F.) at atmospheric pressure. Gentle agitation is used to minimize the possibility of forming water-in-oil emulsions. Preferably, the fatty acid methyl ester-containing phase is washed with from about 5% to about 20% water, more preferably from about 10% to about 15%. The residence time for the water washing phase preferably ranges from about 5 minutes to about 30 minutes, more preferably from about 5 to about 15 minutes. The temperature preferably ranges from about 37.8° C. (100° F.) to about 76.6° C. (170° F.).

The water phase is then separated from the ester phase by conventional means (e.g., gravity or centrifugal force) and the ester phase is analyzed for residual glycerine. If the glycerine level of the fatty acid methyl ester phase is greater than 300 ppm, the water washing step is repeated.

An alternative way to remove glycerine from methyl ester is to adsorb it into solids, e.g. silica gel. From 0.01% to 3% silica gel is mixed with the methyl ester at 21.1° C. (70° F.) to 93.3° C. (200° F.) for 15 to 120 minutes. The silica gel or other solid is removed by filtration or other means.

4. Distillation of Fatty Acid Methyl Ester Phase

The last step in preparing the fatty acid methyl esters in the process of the present invention is the distillation of the fatty acid methyl ester phase under conditions suitable to produce fatty acid methyl esters with a monoglyceride level of less than about 500 ppm, a nondetectable level of di- and triglyceride, and a glycerine level of less than about 200 ppm. Preferably the glycerine level of these fatty acid methyl ester is less than about 100 ppm. More preferably the glycerine level is less than 50 ppm.

Batch (single stage or multistage) or continuous distillation can be used. For batch distillation, residence times typically range from about 4 hours to about 30 hours, preferably from about 6 to about 18 hours, more preferably from about 8 hours to about 12 hours. For continuous distillation, residence times typically range from about 0.1 to about 10 minutes, more typically from about 0.5 to about 5 minutes. Pressures of from about 0.005 to about 30 mm Hg, preferably from about 1 to about 5 mm Hg, are used in the distillation process. Temperatures typically range from about 121.1° C. (250° F.) to about 301.6° C. (575° F.), more typically from about 162.8° C. (325° F.) to about 273.9° C. (525° F.), even more typically from about 232.2° C. (450° F.) to about 260° C. (500° F.).

Since the first distillate is rich in glycerine, a light cut of 2 to 5% by weight of the product is optionally taken first to minimize carryover of glycerine into the distilled methyl ester. Alternatively the first distillate can be pumped back to the still pot to convert the glycerine to mono-, di- or triglycerides. Glycerides, soaps, unsaponifable and other high molecular weight minor components are removed in the heavy cut (still bottoms) of the distillation and methyl ester is removed in the distillate (mid cut).

When single stage, continuous distillation is used, heat treatment is generally necessary prior to distillation to convert monoglyceride to di- or triglyceride in order to prevent volatilization of monoglyceride with methyl ester. No heat treatment is necessary in a multistage continuous distillation process. For batch distillation, heat treatment occurs as part of the first one to four hours of the heat up and distillation process.

The yield of fatty acid methyl esters according to this process is at least about 90%, preferably at least about 94%.

B. Transesterifying the Fatty Acid Methyl Esters and a Polyol

The second step of the process of the present invention comprises transesterification of a fatty acid methyl ester and a polyol. This transestrification reaction can occur in a one step or two step process which can be solvent-based or solvent-free (See, for example, U.S. Pat. No. 4,954,621 (Masaoka et al.); U.S. Pat. No. 4,968,791, (Van Der Plank), issued Nov. 6, 1990; U.S. Pat. No. 5,079,355 (Meszaros Grechke et al.) issued Jan. 7, 1992; or U.S. Pat. No. 5,071,975 (Ver der Plank et al.) issued Dec. 10, 1991, herein incorporated by reference). Preferably the transestrification reaction is a solvent-free two stage transesterification reaction in which polyol fatty acid polyesters having a triglyceride level of less than about 0.5% by weight are formed. Preferably, the polyol fatty acid polyester prepared according to the transesterification reaction contain less than about 0.2% triglyceride, more preferably less than about 0.1%. Such polyol fatty acid polyesters may be considered "fat-free".

When a two stage solvent-free esterification reaction is used to prepare the polyol fatty acid polyesters herein, polyol fatty acid partial esters are first formed from a heterogeneous reaction mixture containing a polyol, at least a portion of the fatty acid methyl esters prepared according to step A hereinabove, an effective amount of a basic esterification catalyst, and optionally, but preferably an emulsifier to improve contact between the sucrose and the methyl esters such as soap and/or sucrose partial esters. Raw materials which are substantially free of glycerine and monoglyceride are selected for use in the process of the present invention. Fatty acid methyl esters which are substantially free of glycerine and monoglyceride are those that are described in step A hereinabove.

As used herein, the term "polyol" is intended to include any linear, cyclic, or aromatic compound containing at least four free esterifiable hydroxyl groups. Suitable polyols include monosaccharides such as, mannose, galactose, arabinose, xylose, ribose, apiose, rhamnose, psicose, fructose, sorbose, tagitose, ribulose, xylulose, and erythrulose; oligosaccharides such as, maltose, kojibiose, nigerose, cellobiose, lactose, melibiose, gentiobiose, turanose, rutinose, trehalose, sucrose and raffinose, and polysaccharides amylose, glycogen, cellulose, chitin, inulin, agarose, zylans, mannan and galactans can also be used in the process of the present invention. The sugar alcohols most widely distributed in nature and suitable for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol, and sucrose. The most preferred is sucrose.

The use of a small particle size polyol, e.g., sucrose, in esterification reactions to form polyol polyesters is highly desirable to improve the speed of reaction. An improved reaction can be achieved without the use of solvent, either in a preliminary step, or in the reaction itself, if the particle size of the solid polyol is less than about 100 microns, preferably less than about 50 microns, more preferably less than about 10 microns. These particle sizes can be achieved, for example, by a combination of grinding, milling, and/or sieving.

Alkali metal soaps are typically, and preferably, used as emulsifiers in the improved process described herein. For solid polyols, like sucrose, such soaps are believed to be essential. As used herein, the term "alkali metal fatty acid soap" is intended to include the alkali metal salts of saturated and unsaturated fatty acids having from about 8 to about 22 carbon atoms, preferably from about 8 to about 18 carbon atoms. Accordingly, suitable alkali metal fatty acid soaps include, for example, the lithium, sodium, potassium, rubidium, and cesium salts of the fatty acids described hereinbefore. Mixtures of fatty acids derived from soybean oil, sunflower oil, safflower oil, and corn oil are preferred for use herein. Accordingly, preferred alkali metal fatty acid soaps include, for example, the potassium soap made from soybean oil fatty acids.

Although some level of soap is typically necessary for optimal performance, especially with solid polyols (e.g. sucrose), the absolute level of soap is desirably kept low, even when there is another emulsifier present. The level of soap should be at least enough to dissolve the polyol at an acceptable rate. Therefore, the level of soap can be reduced as a result of using smaller particle polyol, e.g., sucrose, and/or reaction conditions that favor the solubilization of the polyol. Too much soap can cause excessive foaming. The level of soap in the first stage of the reaction is desirably from about 0.001 to about 0.75, preferably from about 0.1 to about 0.4 moles of soap per mole of polyol. This level of soap assists the polyol, especially sucrose, to dissolve in the reaction mixture. The soap is preferably used in combination with another emulsifier, preferably with the lower esters of the polyol and the fatty acid which are present either by being added as part of the initial reaction mixture, or by backmixing. Also, the soap is preferably potassium soap of hydrogenated fatty acids containing from about 8 to about 22 carbon atoms.

Like the fatty acid ester reactants, it is also highly desirable that the soap contain little or no difatty ketones and/or β-ketoesters. These by-products can form in the soap as the result of contact with basic reagents, such as potassium hydroxide, used during saponification. Preferably, the soap contains about 10 ppm or less difatty ketones and/or β-ketoesters.

Suitable basic catalysts for use in preparing the polyol fatty acid polyesters described in the present invention include alkali metals such as sodium, lithium and potassium, alloys of two or more alkali metals, such as sodium-lithium and sodium-potassium alloys; alkali metal hydrides, such as sodium, lithium and potassium hydride; alkali metal lower ($C_1$–$C_4$) alkyls such as butyl lithium; and alkali metal alkoxides of lower ($C_1$–$C_4$) alcohols, such as lithium methoxide, potassium t-butoxide, potassium methoxide, and/or sodium methoxide. Potassium methoxide is preferred, especially when used with potassium soap. Certain basic catalysts, such as sodium and potassium hydride, are particularly prone to generate difatty ketones and/or β ketoesters.

Another particularly preferred class of basic catalyst includes potassium carbonate, sodium carbonate, barium carbonate, or mixtures of these compounds having particle sizes that are less than about 100 microns, preferably less than about 50 microns, as discussed more fully hereinafter. It has been found that when these specific compounds are used as catalysts, increased yields of light colored higher polyol polyesters are obtained when compared to essentially identical reactions carried out using more conventional catalysts, such as sodium hydride, potassium hydride, soap, or sodium methoxide. These preferred catalysts can also be used in admixture with the more conventional basic catalysts, described above. Potassium carbonate and/or potassium methoxide are the most preferred catalysts for use herein. The use of these catalysts is further disclosed in U.S. Pat. No. No. 4,517,360 (Volpenhein), issued May 14, 1985, which is incorporated herein by reference.

More reactive catalysts such as potassium or sodium methoxide can be protected until their addition into the reaction mixture. Preferably the catalyst should be suspended in or more preferably encapsulated by a material that will either be present in the reaction mixture or be readily separated from the reaction mixture. Suitable encapsulating agents include said alkyl esters of, e.g., $C_{16}$–$C_{22}$ fatty acids. (As described hereafter, these catalysts can also be protected when prepared from and stored in a lower ($C_1$–$C_4$) alcohol, such as methanol, under anhydrous conditions.) Addition of these more alkaline, reactive catalysts in the second stage of the reaction after the polyol has an average degree of esterification of more than about 60%, preferably more than about 85%, provides improved reaction kinetics and results in a greater degree of esterification of the polyol yet does not create the level of color/odor materials that would be created if such catalysts were present from the start of the reaction.

The level of catalyst is kept as low as possible, particularly in the second stage of the reaction, as discussed more fully hereafter, typically in the range of from about 0.01 to about 0.5, preferably from about 0.01 to about 0.1, more preferably from about 0.02 to about 0.05, moles of catalyst per mole of polyol. The level of catalyst can be lowered to the least amount that is effective to give a reasonable rate of reaction. It is possible to have very fast reactions using only the residual base in, e.g., the soap emulsifier commonly used in such reactions. It is desirable to keep the level of base as low as possible to minimize formation of color and/or odor bodies and/or excess soap and/or by-products. It is also desirable to effect the removal of oversize catalyst after the first stage of the reaction, and/or the destruction and removal of the catalyst after the reaction has reached the desired end point.

Typically, the molar ratio of the fatty acid methyl esters to the polyol ranges from about 8:1 to about 13.5:1. If soap is used as an emulsifier, the molar ratio of the soap to the polyol typically ranges from about 0.08:1 to about 0.75:1. If sucrose partial esters are used as emulsifiers, they can be added to the starting mixture at a level of 1% to 50% by weight, preferably 5% to 30%, more preferably 10% to 20%. Combinations of sucrose esters and soap can be used advantageously. The ratio of catalyst to the polyol typically ranges from about 0.02:1 to about 0.2:1. The precise ratio of these reactants can be freely selected from within the guidelines previously described. However, some routine experimentation can be necessary in order to establish the optimum ratios for a given set of reactants. The first stage reaction mixture can be formed in a solvent-free manner or by using a solvent such as water to dissolve one or more of the reactants (e.g., sucrose), followed by removal of the solvent before carrying out the first stage reaction.

This first stage reaction mixture is then heated to an appropriate temperature to provide a melt in which the polyol and the fatty acid methyl esters react to form polyol fatty acid partial esters. As used herein, the term "polyol fatty acid partial esters" are those esters of the polyol wherein up to about 50% of the hydroxy groups of the polyol have been esterified. In the case of sucrose, the primary sucrose fatty acid partial esters are the mono-, di- and/or triesters. The end of the first stage of the reaction is usually determined by measuring the level of unreacted polyol in the reaction mixture. In the case of sucrose, the end of the first stage typically occurs when the level of unreacted sucrose is less than about 1%.

This first stage reaction mixture is typically heated to temperatures of from about 265° to about 285° F. (from about 129.4° to about 140.6° C.), preferably to from about 270° to about 275° F. (from about 132.2° to about 135° C.). These reaction temperatures typically achieve a rapid initial esterification of the polyol to form the polyol fatty acid partial esters without excessive degradation of the polyol. The first stage reaction is also desirably carried out under a pressure of from about 1 to about 100 mm Hg, preferably from about 5 to about 50 mm Hg.

If soap is the emulsifier, after the average degree of esterification reaches about 60%, the soap emulsifier is no longer needed to facilitate the reaction and, therefore, can be removed. The soap emulsifier is not essential after the polyol has reacted once and there is sufficient partial ester to maintain the homogeneity of the reaction mixture. Removal of soap can be accomplished, e.g., by filtration, centrifugation, etc., since the soap is relatively insoluble in the reaction mixture at higher degrees of esterification. The filtered reaction mixture typically has a soap level of less than about 0.5, preferably less than about 0.1 moles of soap per mole of polyol, more preferably less than about 0.05 moles of soap per mole of polyol. The filtered material can be used as a reactant in the first stage reaction mixture. However, since the composition of the filtered material can vary, it is usually better not to recycle it.

Unreacted polyol and/or large particle catalyst are also desirably removed from the reaction mixture via filtration and/or centrifugation.

In the second stage of the solvent-free transesterification reaction, highly esterified polyol fatty acid polyesters are formed from a reaction mixture containing the polyol fatty acid partial esters, the remaining portion of the fatty acid methyl esters, and an effective amount of a basic catalyst. This remaining portion of the fatty acid methyl esters can be obtained by including an excess thereof in the first stage reaction mixture, i.e. an amount beyond that required to form polyol fatty acid partial esters ("single-step" addition). However, the remaining portion of the fatty acid methyl esters required to obtain highly esterified polyol fatty acid polyesters is typically added to the reaction mixture resulting from the first stage of the reaction ("two-step" addition).

The reaction mixture resulting from the first stage of the reaction can contain sufficient basic catalyst for the purposes of the second stage of the reaction. However, more basic catalyst can be added, if needed. This additional basic catalyst can be the same as the basic catalyst used in the first stage of the reaction, or can be a different basic catalyst.

During the second stage of the reaction, the polyol fatty acid lower esters and the remaining portion of the fatty acid esters react to provide highly esterified polyol fatty acid polyesters. As used herein, the term "highly esterified polyol fatty acid polyesters" refers to a polyol wherein at least about 50%, preferably at least about 70%, and most preferably at least about 96%, of the hydroxy groups are esterified. In the case of highly esterified sucrose polyesters, this typically refers to the hexa-, hepta-, and particularly octa-esters. For example, if at least about 96% of the hydroxy groups of sucrose are esterified, at least about 70% of the sucrose esters are sucrose octaesters.

The use of the fatty acid methyl esters prepared in step A of the process of the present invention in the transesterification reaction described in step B of the process of the present invention results in the formation of polyol fatty acid polyesters which have levels of triglyceride of less than about 0.5% by weight. Preferably, these polyol fatty acid polyesters have triglyceride levels below about 0.2%, more preferably below about 0.1%. Such polyol fatty acid polyesters may be considered fat-free.

ANALYTICAL TEST METHODS

A number of parameters used to characterize elements of the present invention are quantified by particular experimental analytical procedures. Each of these procedures is described in detail as follows:

LEVEL OF GLYCERINE AND MONO-, DI-, AND TRIGLYCERIDES (PPM) BY SFC

Scope

This method is applicable to the determination of glycerine and mono- di- and tri- glycerides in methyl esters and the determination of triglyceride levels in polyol polyesters. The method is used to monitor the completeness of the transesterification reaction of triglycerides to methyl esters and to measure triglyceride levels in polyol polyesters made from the methyl esters.

Principle

An internal standard is added to a weighed sample of methyl esters or polyol polyester. Silylating agents are then added to the sample to derivatize the glycerine and free hydroxyls and any fatty acids present in the sample. The sample is filtered and then is injected onto a 10M DB-1 capillary column in a Supercritical Fluid Chromatograph.

The separation is based on molecular weight and detection is by a flame ionization detector. The level of glycerine and/or glycerides is calculated using an internal standard calculation based on the areas of all the glycerine/glyceride peaks and the internal standard determined by the integrator. An experimentally determined response factor is utilized.

| APPARATUS | |
|---|---|
| SFC Gas Chromatograph | Lee Scientific, model 602, Equipped with 0.1 µl injection valve and split flow injection, FID, and Spectra Physics SP4270 integrator (or equivalent) |
| DB1 Capillary Column | 10 m O.D. × 50µ I.D., 0.2µ Film, DB1, J&W Scientific |
| Vials | 2 or 4 ml, Kimble Glass, Fischer Scientific #03-340-1c |
| Disposable syringe | 5.0 ml Fisher Scientific |
| Filter | 0.45µ Alltech Associates |
| Hot Plate | Corning #PC-35 or equivalent |
| Analytical Balance | 4 decimal place readout |

| REAGENTS AND SOLVENTS | |
|---|---|
| $CO_2$ | SFC grade, Scott Specialty Gases |
| $C_{22}$ Methyl Ester | Fluka, Cat. #11940 |
| BSTFA (bis(trimethylsily)-(trifluoroacetamide) | Supelco, Cat. #3-3027 |
| Molecular Sieve, Grade 514, Type 4A | Fisher #M514-500 |
| Pyridine | ACS Grade MCB #PX2020-01 |
| Glycerine | USP-Glycerine-Superol Procter and Gamble CD Standards Lab SWTC |
| TMSI (trimethyl silylimidazole) | Supelco, Cat. #3-3068 |

| SFC CONDITIONS | |
|---|---|
| Oven temperature | 90° C. |
| Detector temperature | 350° C. |
| Pressure program | 100–375 atm @10 atm/min., hold at 375 atm for 10 min. |
| CO2 (column) | 5–8 ml/min. at 300 atm. |
| Hydrogen | ~40 ml/min. |
| Air | ~400 ml/min. |
| Auxiliary Gas (nitrogen) | ~25 ml/min. |

Preparation of Internal Standard Solution

Weigh about 0.05 grams to (±0.0001 g) of methyl Dodecanoate into a 100 ml volumetric flask. Dilute to volume with dry pyridine (Note: pryidine dried over molecular sieve type 4A) Mix well and label as ISTD.

Preparation of Standard Solutions

In order to determine the response factor, standard solutions of glycerine and glycerides are prepared in methyl ester and in polyol polyester. For methyl ester, stock solutions of 100 ppm, 250 ppm, 500 ppm, and 1000 ppm of glycerine and C18 monoglyceride, diglyceride and triglyceride are prepared using a methyl ester substrate substantially free of these components. For polyol polyesters, the same stock solutions of C18 triglyceride are prepared using a pure polyol polyester substrate.

SFC Sample Preparation

Weigh about 0.04 grams (to an accuracy of ±0.0001 g) of thoroughly mixed standard solution into a 2 dram vial. Accurately add 1 ml of internal standard solution and 1 ml of 5:1 TMSI/BSTFA to sample and cap loosely (1 part BSTFA added to 5 parts TMSI). Place sample in a heating block on hot plate at 90° C. for approximately 15 minutes. Inject the silyated sample into the SFC.

Response Factor Calculation

The chromatograms from each of the standard solutions are used to determine a response factor (RF) as follows:

$$RF = \frac{\text{Area of Internal Standard}}{\text{Total Area of Glycerine/Glyceride}} \times \frac{\text{Weight of Glycerine/Glyceride (gr)}}{\text{Weight of Internal Standard (gr)}}$$

Methyl Ester/Polyol Polyester Sample Analysis

Prepare the sample as described above in "SFC sample preparation". Calculate the amount of glycerine/glyceride present as follows:

$$\text{PPM Glycerine/Glyceride} = \frac{\text{Total Area of Glycerine/Glyceride}}{\text{Area of Int. Std.}} \times \frac{\text{Weight of Int. Std. (gr)}}{\text{Weight of Sample (gr)}} \times RF \times 1{,}000{,}000$$

2. LEVEL OF GLYCERIDES IN METHYL ESTERS BY HIGH TEMPERATURE GAS CHROMATOGRAPHY (HTGC)

Scope

This method is applicable for the determination of mono-, di-, and triglycerides in methyl esters. The method is for the determination of completeness of the transesterification of fat to methyl esters. Relative standard deviation of this method =10.3%.

Principle

A sample of methyl esters is silylated to derivatize any fatty acids and glycerides present. The sample is injected onto a 15M DB-1 capillary column. The methyl esters and glycerides are separated by chain length. The level of glycerides is determined by their area percents.

| EQUIPMENT AND CONDITIONS | |
|---|---|
| Gas Chromatograph | HP 5890 or equivalent with capillary injection port, FID, HP 3393A integrator, and 7673A autosampler |
| Syringe | 50 µL Harffilton 10 ul Hamilton, model #701N Supelco Catalog #2-0734 |
| 4 dram vials | Kimble Glass Fisher Scientific #03-340-1C |
| GC vials | Supelco #3123 |
| Caps | Supelco #3-3116 |
| Crimper | Supelco #3-3195 |
| Capillary Column | DB-1-15N, 0.25u film; J&W Scientific #122-1012 |
| Hot Plate | 90° C. Corning #PC-35 or equivalent |

| REGENTS AND SOLVENTS | |
|---|---|
| BSTFA | Supelco cat. #3-3027 |
| TMSI | Supelco cat. #3-3068 |
| Pyridine | ACS Grade MCB #PX2020-01 |
| Mol. Sieve, Type 4A | Fisher #M514-500 |
| Monoolein | Nu-Check-Prep Inc. Cat. #M-239 |

-continued

| REGENTS AND SOLVENTS | |
|---|---|
| Diolein | Nu-Check-Prep Inc. Cat. #D-236 |
| Monopalmitin | Nu-Check-Prep Inc. Cat. #M-154 |
| Dipalmitin | Nu-Check-Prep Inc. Cat. #D-151 |
| Monostearin | Nu-Check-Prep Inc. Cat. #M-164 |
| Distearin | Nu-Check-Prep Inc. Cat. #D-161 |

| GC CONDITIONS | |
|---|---|
| Column Head Pressure | ~10 psi |
| Septum purge flow | 0.5–2 ml/minute |
| Spilt Vent Flow | ~70 ml/minute |
| Initial Temp | 150° C. |
| Initial Time | 0 minutes |
| Rate | 10° C./minute |
| Final Temp | 350° C. |
| Final Time | 10 minutes |
| Inj. Temperature | 280° C. |
| Det. Temperature | 360° C. |
| Chart Speed | 1 cm/minute |
| Attenuation (GC) | 0 - Has no effect when 3393A |
| Range | 0 - integrator is used |
| % Offset | 10% |
| Peak Width | 0.04 |
| Threshold | 0 |
| Attenuation (integrator) | 2 |
| Range (integrator) | 0 (Has no effect when 3393A integrator is used) |
| Aux. Flow rate + Column Flow | 30 mL/minute |
| Air pressure | 40 psi |
| Air flow rate | 400 ml/minute |
| Hydrogen Pressure | Approx. 18 |
| Hydrogen Flow Rate | 30 minute |
| INJ. Volume | 2 µl |

Preparation of Derivatizing Regent

Mix 5 parts TMSI with 1 part BSTFA. Store in a tightly capped bottle.

Glyceride Stock Mixture Preparation

Prepare a glyceride standard stock mixture by accurately weighing 0.2 g of each of the following glycerides into a 4-dram vial:

1) Monoolein
2) Diolein
3) Monopalmitin
4) Dipalmitin
6) Disstearin

Mix thoroughly. Label as glyceride stock mixture. This mixture should be stored in the refrigerator.

Standard Preparation

Melt glyceride standard stock mixture and accurately weigh 0.1 g into a 4-dram vial. Add 9.9 grams of liquid cottonseed or liquid soybean methyl esters. Mix well. This should produce a 1% glyceride standard. Using a glass pasteur pipet, put one full drop of the standard into a GC vial. Add 0.5 mL of the derivatizing reagent and 0.5 ml pyridine. Cap the vial and warm on hot plate at 75°–80° C. of approximately 15 minutes. Inject the sample into the GC. Inspect the chromatogram and identify the mono- and diglycerides. Sum the area percents of the glyceride peaks. The percent glycerides should be within the established limits. A standard should be prepared and run with each batch of samples.

Sample Preparation

Using a glass pasteur pipet, place one full drop of sample into a GC vial. Add 0.5 mL of the derivatizing reagent and 0.5 ml pyridine. Cap the vial and heat on hot plate at 75°–80° C. for approximately 15 minutes. Do not overheat.

The percent glycerides is based on the area percent as follows:

$$\% \text{ Glycerides} = \frac{\text{Sum of the Glyceride Component Areas}}{\text{Total Peak Areas}} \times 100$$

3. % OCTAESTER BY HPLC

Scope

This method measures the distribution of sucrose esters in a sucrose polyester sample at levels greater than 50% octaester. It is not suitable for use with samples containing octaester at levels below this value because of the limited solubility of the lower polyesters in the solvent system used. The standard deviation at the 70% octaester level is 0.7%. This method is applicable to sucrose polyesters made from cottonseed and soybean esters.

Principle

The sucrose polyester sample is dissolved in hexane, filtered, and injected into the HPLC, where the normal phase separation of the sucrose polyester based on the number of free hydroxyl groups takes place. All esters lower than pentaester are lumped together. Detection is by a light-scattering mass detector. The octaester level is calculated by the integrator as the normalized octaester area percent.

| Apparatus | Notes |
|---|---|
| LC system | HP-1090 with DR5 pumps, variable volume injector, autosampler, heated column compartment, column switching valve Hewlett-Packard |
| Model 3392A Computing Integrator | |
| Light scattering mass detector | Applied Chromatography Systems #750/14 |
| 80 mm × 4 mm, 5 um Zorbax Refiance Silica Column | Zorbax Reliance, DuPont #820662-931 |
| LC guard column | Zorbax Reliance, DuPont 820674-931 |
| LC Hardware | Zorbax Reliance, DuPont 820678-901 |
| Column inlet filter | Rheodyne #7335RV |
| Replacement filter discs | Rheodyne #7335-010 |
| Regents | |
| Hexane (UV Grade) | Burdick & Jackson (#216) or J. T. Baker (HPLC grade) 9304-03 |
| Methyl-t-Butyl Ether (UV Grade) | Burdick & Jackson (#242) |
| Nitrogen (40 psi minimum) | Dried and Filtered |
| Air (80 psi) | |
| Equipment | |
| 4-Dram vials with caps | Fisher Scientific |
| Disposable pipets | |
| Repiper dispenser (5 ml) | |
| Disposable 0.45 um Filter Discs | Gelman Acrodisc or equiv. |
| Hot plate | |
| 5-mL disposable syringes | |
| GC vials (1.5 mL) with caps and crimper | Supelco, Fisher Scientific |

-continued

| BPLC Conditions | Gradient Program | |
|---|---|---|
| Mobile Phase: | Time | % B |
| A = Hexane | 0 min. | 4.8 |
| B = Methyl-t-Butyl Ether | 4.8 | 4.8 |
|  | 5.1 | 16 |
| FLOW 2.0 ml/min | 8 | 16 |
| Maxpress = 400 | 8.1 | 25 |
| Minipress = 0 | 10 | 25 |
| Oven temp = 37° C. | 10.0 | 50 |
| Inj. Vol. = 20 ul | 12 | 50 |
| Slowdown = 5 | 12.1 | 100 |
| Stop time = 15.5 min. | 15 | 100 |
| Post time = 8 min. | 15.5 | 0 |
| Column Switch = 0 | | |

| Detector Conditions | Integrator conditions | |
|---|---|---|
| Pressure = 15–20 psi | Atten = 6 | |
| Temperature = 59° C. | Chart speed = 0.5 | |
| Range = 8 | Peak width = 0.3 | |
| Photomultiplier = 2 | Threshold = 3 | |
| Time constant = 5 sec. | Area reject = 1000 | |
|  | Time 0.1 | Intg # = 9 |
|  | Time 0.1 | Intg # = 15 |
|  | Time 1.25 | Intg # = –9 |
|  | Time 15.00 | stop |

Sample Preparation

1. Melt the sucrose polyester sample to be analyzed if needed, shake gently and piper 0.17 g into a 4 dram vial. Add 10 mL of hexane, cap the vial and shake to dissolve. Gently warm the sample if the sucrose polyester is a solid to help it dissolve.
2. Assemble a 0.45µ filter and a 5 ml syringe. Filter about 2 mL of the solution into GC vial.
3. Firmly crimp the vial and load it into the autosampler single vial injector arm and inject the sample.

Calculations

The % octaester result is based on the normalized area percents of the sucrose polyester peaks.

EXAMPLES

Example I

Synthesis of Methyl Esters

Peanut oil triglyceride (4,026 lbs.) is mixed with methanol (650 lbs.) and sodium methoxide solution (73 lbs. of 25% NaOCH$_3$ in methanol) for about one hour at 65° C. in a stirred tank reactor. At the end of that time, agitation is stopped and the glycerine layer is allowed to settle for one hour. The glycerine (723 lbs.) is drained from the bottom of the reactor. A second esterification lo reaction is done by adding 60 lbs. of methanol and 11.3 lbs. of the sodium methoxide solution and mixing for one hour at 65° C. in a stirred tank reactor. Agitation is stopped and the glycerine layer is settled and removed as above (33 lbs.). The composition of the ester layer after the second extraction is 0.48% monoglycerides, 0.08% diglycerides and 1.45% glycerine as determined by Analytical Method # 2.

The ester layer is washed with 1,505 lbs. of deionized water for 10 minutes at 65° C. using a low rate of stirring to minimize the formation of water-in-oil emulsion. After the agitation is stopped, the water layer is allowed to settle for one hour. The water layer (1,692 lbs.) is drained from the bottom of the reactor. A second water wash, agitation, settling and removal is done using the same process conditions and amount of water. The composition of the crude ester after the second water wash is 0.487% monoglycerides, 0.08% diglycerides and 222 ppm glycerine as determined by Analytical Method # 2.

The ester is distilled by using a one-stage batch distillation process. A vacuum of 1 mm Hg of mercury is used in the reaction vessel and the temperature is slowly increased to a temperature to 160° C. (320° F.). The first distillate is rich in glycerine, and is pumped back to the still pot to be converted to mono-, di- or tri- glycerides during the batch distillation. If the distillate appears watery, it is pumped to a separate storage vessel. The reactor temperature is slowly increased from 160° C. (320° F.) to 182.2° C. (360° F.) over a 21 hour period to obtain a maximum yield of distillate. A total of 3,555 lbs. of distillate is obtained along with a distillate residue of 140 lbs. The residue is 4% by weight of the combined distillate and residue. The composition of methyl ester after distillation is 430 ppm monoglyceride, <50 ppm di- and tri- glycerides and 70 ppm glycerine as determined by Analytical Method # 1.

Synthesis of Polyol Polyester

The methyl ester (1,317 lbs.) is mixed with 200 lbs. of potassium stearate, 300 lbs of granular sucrose and 12 lbs. of granular potassium carbonate in a 750 gallon reactor for 7.5 hours at a temperature of 135° C. and a pressure of 1–10 mm Hg. Additional methyl ester (2,095 lbs.) and granular carbonate (12 lbs.) are added to the reactor and mixed for another 5 hours at 135° C. and a pressure of 1 to 4 mm Hg until the composition of the polyol polyester is 74.9% octaester, 24.8% heptaester and 0.25% hexaester and below.

The soap is removed by adding 211 lbs. if deionized water at 77° C. in a 750 gallon stirred tank reactor and centrifuging. Color and lower levels of soap are removed by water washing with 629 lbs. of deionized water at 77° C. in a stirred tank reactor for 10 minutes at low rpm. The water is settled for one hour by gravity and then drained from the bottom of the reactor. The product is dried by reducing the pressure to <10 mm Hg and maintaining the temperature at 65°–80° C. Silica gel (35 lbs.) is mixed with the dry product at 77° C. for 30 minutes. The silica gel is removed in a filter press and the product is then evaporated at a temperature of 235° C. (455° F.) at a pressure 1.0 mm Hg, and finally steam stripped with 10% steam in a packed column at a temperature of 235° C. (455° F.) and a pressure of 2 mm Hg.

The triglyceride level in the finished product is 0.37% as determined by a Analytical Method # 1.

Example II

Synthesis of Methyl Esters

Touch hardened soybean oil triglyceride (47,310 lbs) is mixed with methanol (10,400 lbs) and sodium methoxide solution (662 lbs of 25% NaOCH$_3$ in methanol) for about one hour at 65° C. in a stirred tank reactor. Agitation is stopped an the glycerine layer is allowed to settle for one hour. The glycerine is drained from the bottom of the reactor. A second esterification is done by adding another 213 lbs of the sodium methoxide solution and mixing for one hour at 65° C. in a stirred tank reactor. Agitation is stopped and the glycerine layer is settled and removed as above.

The ester layer is washed twice with 2365 lbs. of softened water for 10 minutes at 65° C. using a low rate of stirring to minimize the formation of water-in-oil emulsion. After each wash the agitation is stopped and the mixture is allowed to settle for 1.5 hours. Then the water layer is drained from the bottom of the reactor.

The ester is distilled by using a multi-stage batch distillation process. A vacuum of 10 mm Hg of mercury is used in the reaction vessel and the temperature is slowly increased to a temperature of 232.2° C. (450° F.) The vaporized methyl ester travels through a packed column with ten actual separation stages and in then condensed. A reflux ratio of 0.5:1 or less is used on the column to prevent the entrainment of heavy molecular weight components in the distillate. The first distillate is rich in glycerine, so a top cut of 1100 lbs is removed and scrapped. After the top cut, the distillate is water white in appearance. The reactor temperature is slowly increased from 232.2° C. (450° F.) to 260° C. (500° F.) over a 12 hour period to complete the distillation. Approximately 43,000 lbs. of distillate is obtained along with a distillate residue of approximately 1,000 lbs. The residue is 2.3% by weight of the combined distillate and residue. The composition of methyl ester after distillation is 160 ppm monoglyceride, nondetectable di- and tri- glycerides and 55 ppm glycerine as determined by Analytical Method # 1.

Synthesis of Polyol Polyester

Five batches of polyol polyester are made in the 750 gallon reactor with the methyl ester described in this Example III. The methyl ester (1,522 lbs.) is mixed with 200 lbs. of potassium stearate, 350 lbs of granular sucrose and 2.8 lbs. of powdered potassium carbonate for 4 to 5.5 hours at a temperature of 135° C. and a pressure of 1–20 mm Hg. Additional methyl ester (1827 lbs.) and powdered potassium carbonate (2.8 lbs.) is added in the reactor and is mixed for another 4.5 to 7 hours at 135° C. and a pressure of 1 to 5 mm Hg until the composition of the polyol polyester is 72 to 77% octaester, with the remainder being primarily heptaester.

All five reaction batches are combined and the soap is removed by hydrating with 1275 lbs. of deionized water and centrifuging. The mixture is washed with 2775 lbs of deionized water with tripotassium citrate chelant added for 10 minutes at low rpm. Agitation is stopped and the mixture is allowed to settle for one hour. The water is then drained from the bottom of the reactor. A second water washing is done with 2770 lbs of deionized water and chelant. The mixture is again allowed to settle and the water is removed. The product is dried under a tank pressure of <10 mmHg and a temperature of 65°–80° C. Silica gel (150 lbs.) is mixed with the dry product at 82° C. for two hours. The silica gel is removed in a filter press and the product is then evaporated at a temperature of 215.5° C. (425° F.) at a pressure <1 mm Hg, and finally steam stripped with 10% steam in a packed column at a temperature of 215.5° C. (425° F.) and a pressure of 4 mm Hg.

The triglyceride level in the finished product is 0.18% ppm as determined by Analytical Method # 1.

What is claimed:

1. A process for preparing fat-free nondigestible polyol fatty acid polyesters, which process comprises the steps of:
   A. preparing fatty acid monohydric lower alkyl esters having a level of monoglycerides below 500 ppm, a non-detectable level of di- and triglyceride and a glycerine level below 200 ppm by (1) reacting a fatty acid glycerol ester with a monohydric lower alkyl alcohol in the presence of a suitable catalyst to produce a mixture of fatty acid monohydric lower alkyl esters, fatty acid glycerol esters and glycerol; (2) separating the mixture produced in step (1) into a glycerine phase and a fatty acid monohydric lower alkyl ester-containing phase which fatty acid monohydric lower alkyl ester-containing phase has a level of residual mono-, di-, and triglycerides below 2.5%; (3) water washing the fatty acid monohydric lower alkyl ester-containing phase under conditions suitable to provide a fatty acid monohydric lower alkyl ester phase containing less than 300 ppm glycerine, and (4) distilling the fatty acid monohydric lower alkyl esters under conditions suitable to provide fatty acid monohydric lower alkyl esters having a level of monoglycerides below 500 ppm, a non-detectable level of di- and triglyceride and a glycerine level below 200 ppm; and
   B. transesterifying the fatty acid monohydric lower alkyl esters and a polyol to provide a polyol fatty acid polyester having a triglyceride level of less than 0.5% in a solvent-free two-stage process wherein the first stage comprises forming polyol fatty acid partial esters from a reaction mixture containing a polyol having more than 4 esterifiable hydroxy groups and at least a portion of the fatty acid esters of the easily removable alcohol in the presence of an effective amount of a basic catalyst and optionally an effective amount of soap emulsifier, and wherein the second stage comprises forming highly esterified polyol fatty acid polyesters from a reaction mixture containing the polyol fatty acid partial esters, the remaining portion of the fatty acid esters and an effective amount of a basic catalyst.

2. A process for preparing fat-free nondigestible polyol fatty acid polyesters according to claim 1 wherein in step (A) the yield loss from still bottom residue is less than 10%.

3. A process for preparing fat-free nondigestible polyol fatty acid polyesters according to claim 1, wherein the fatty acid glycerol ester in step (A)(1) is a triglyceride and the monohydric lower alkyl alcohol in step (A)(1) is methanol.

4. A process for preparing fat-free nondigestible polyol fatty acid polyesters according to claim 3 wherein step (A) results a yield of at least about 90% fatty acid methyl esters after ester distillation.

5. A process for preparing fat-free nondigestible polyol fatty acid polyesters according to claim 4 wherein the water washing in step (A)(3) occurs under conditions suitable to provide a fatty acid methyl ester-containing phase containing less than 100 ppm glycerine.

6. A process for preparing fat-free nondigestible polyol fatty acid polyesters according to claim 5 wherein in step (A)(3) the fatty acid methyl ester-containing phase is washed with from about 2% to about 50% by weight water in a stirred tank, a column or an in-line static mixer with a residence time of from about 0.5 to about 60 minutes at a temperature of from about 21.1° C. to about 93.3° C. at atmospheric pressure.

7. A process for preparing fat-free nondigestible polyol fatty acid polyesters according to claim 6 wherein in step (A)(4) the distillation occurs at a pressure of from about 0,005 mm Hg to about 30 mm Hg and a temperature of from about 121.1° C. to about 301.6° C.

8. A process for preparing fat-free nondigestible polyol fatty acid polyesters according to claim 7 wherein the nondigestible polyol polyesters product contains less than about 0.2% triglycerides.

9. A process for preparing fat-free nondigestible polyol fatty acid polyesters, which process comprises the steps of:
   A. preparing fatty acid methyl esters having a level of monoglycerides below 500 ppm, a non-detectable level of di- and triglyceride and a glycerine level below 200 ppm by (1) reacting a fatty acid glycerol ester with a methyl alcohol in the presence of a suitable catalyst to produce a mixture of fatty acid methyl esters, fatty acid glycerol esters and glycerol; (2) separating the mixture produced in step (1) into a glycerine phase and a fatty acid methyl ester-containing phase which fatty acid methyl ester-containing phase has a level of residual monoglycerides below 2.5% and a non-detectable level of di-or triglycerides; (3) washing the fatty acid methyl ester-containing phase with from about 2% to about 50% by weight water in a stirred tank, a column or an in-line static mixer with a residence time of from about 0.5 to about 60 minutes at a temperature of from about 21.1° C. to about 93.3° C. at atmospheric pressure; (4) separating the water phase from the ester phase to produce an ester phase having a level of glycerin below 300 ppm; and (5) distilling the fatty acid methyl esters at a pressure of from about 0.005 mm Hg to about 30 mm Hg and a temperature of from about 121.1° C. to about 301.6° C.; and B. transesterifying the fatty acid methyl esters and a polyol in a solvent-free, two-stage process to provide a polyol fatty acid polyester containing less than about 0.5% triglycerides, wherein the first stage comprises forming polyol fatty acid partial esters from a reaction mixture containing a polyol having more than 4 esterifiable hydroxy groups and at least a portion of the fatty acid esters of the easily removable alcohol in the presence of an effective amount of a basic catalyst and optionally an effective amount of soap emulsifier, and wherein the second stage comprises forming highly esterified polyol fatty acid polyesters from a reaction mixture containing the polyol fatty acid partial esters, the remaining portion of the fatty acid esters and an effective amount of a basic catalyst.

10. A process for preparing fat-free nondigestible polyol fatty acid polyesters according to claim 9 wherein the fatty acid glycerol ester in step (A)(1) is a triglyceride.

11. A process for preparing fat-free nondigestible polyol fatty acid polyesters according to claim 10 wherein in step (A)(3) the fatty acid methyl ester-containing phase is washed with 10% to 15% water for from about 5 to about 15 minutes at from about 37.8° C. to about 76.6° C.

12. A process for preparing fat-free nondigestible polyol fatty acid polyesters according to claim 11 wherein in step (A)(5) the fatty acid methyl esters are distilled at a pressure of from about 1 to about 5 mm Hg and a temperature of from about 232.2° C. to about 260° C.

13. A process for preparing fat-free nondigestible polyol fatty acid polyesters according to claim 12 wherein in step (A) the yield loss from still bottom residue is less than 10%.

14. A process for preparing fat-free nondigestible polyol fatty acid polyesters according to claim 13 wherein step (A) results a yield of at least about 90% fatty acid methyl esters after ester distillation.

* * * * *